(12) United States Patent
Connelly et al.

(10) Patent No.: US 9,375,430 B2
(45) Date of Patent: Jun. 28, 2016

(54) MONOACYLGLYCEROL LIPASE INHIBITORS FOR THE TREATMENT OF METABOLIC DISEASES AND RELATED DISORDERS

(71) Applicant: Janssen Pharmaceutica NV, New Brunswick, NJ (US)

(72) Inventors: Margery Connelly, Lansdale, PA (US); Christopher M. Flores, Lansdale, PA (US); Mark J. Macielag, Gwynedd Valley, PA (US)

(73) Assignee: Janssen Pharmaceutica NV, Beerse (BE)

( * ) Notice: Subject to any disclaimer, the term of this patent is extended or adjusted under 35 U.S.C. 154(b) by 0 days.

(21) Appl. No.: 13/628,452

(22) Filed: Sep. 27, 2012

(65) Prior Publication Data

US 2013/0085130 A1    Apr. 4, 2013

Related U.S. Application Data

(60) Provisional application No. 61/541,403, filed on Sep. 30, 2011.

(51) Int. Cl.
| | | |
|---|---|---|
| A61K 31/397 | (2006.01) | |
| A61K 31/00 | (2006.01) | |
| A61K 31/496 | (2006.01) | |

(52) U.S. Cl.
CPC .................................. *A61K 31/496* (2013.01)

(58) Field of Classification Search
USPC .............................. 514/210.18, 909, 910, 911
See application file for complete search history.

(56) References Cited

U.S. PATENT DOCUMENTS

| | | | | |
|---|---|---|---|---|
| 2009/0082435 A1* | 3/2009 | Piomelli et al. | ................ | 514/488 |
| 2010/0041651 A1* | 2/2010 | Even et al. | .................. | 514/234.2 |
| 2010/0197708 A1* | 8/2010 | Talley et al. | ................... | 514/269 |
| 2010/0324014 A1* | 12/2010 | Bian | .................... | C07D 205/04 514/210.18 |
| 2011/0071162 A1* | 3/2011 | Even et al. | ............... | 514/253.04 |

FOREIGN PATENT DOCUMENTS

| | | |
|---|---|---|
| WO | 2008/145843 | 12/2008 |
| WO | 2009/117444 | 9/2009 |
| WO | 2010/124082 | 10/2010 |

OTHER PUBLICATIONS

Grundy, S.M., Metabolic Complications of Obesity. Endocrine, vol. 13, pp. 155-165. Published 2000.*
Taschler, U., et al. Journal of Biological Chemistry vol. 286, pp. 17467-17477, published online Mar. 23, 2011.*
Greenfield, J.R., et al. Clinics in Dermatology. vol. 22, pp. 289-295. Published 2004.*
Nerve Pain in Diabetes: http://www.diabetes.co.uk/diabetes-complications/diabetic-nerve-pain.html. (2013).*
Reagan-Shaw, S. et al., FASEB J vol. 22, pp. 659-661. Published 2007.*
Taschler et al., (Journal of Biological Chemistry, vol. 286, pp. 17467-17477 published online Mar. 23, 2011).*
Greenfield et al, (Clinics in Dermatology, vol. 22, pp. 289-295, published 2004).*
Taschler, U. et al., J. Biol. Chem. vol. 286, pp. 17467-17477. Published online Mar. 23, 2011.*
Taschler and coworkers (Journal of Biological Chemistry, vol. 286, pp. 17467-17477 published online Mar. 23, 2010).*
Wall et al., "A novel poxvirus gene and its human homolog are similar to an *E. coli* lysophospholipaase.", Virus Res., 1997, pp. 152-167, vol. 52.
Dinh et al., "Brain monoglyceride lipase participating in endocannabinoid inactivation.", Proc. Nat. Acad. Sci., 2002, pp. 10819-10824, vol. 99.
Schlossburg et al., "Chronic monoacylglycerol lipase blockade causes functional antagonism of the endocannabinoid system.", Nat. Neurosci., 2010, pp. 1113-1119, vol. 13(9).
Chon et al., "Over-expression of monoacylglycerol lipase (MGL) in mouse small intestine results in an obese phenotype.", FASEB, 2008, pp. 807.12, vol. 22.
Taschler et al., "Monoglyceride Lipase-deficiency in Mice Impairs Lipolysis and Attenuates Diet-Induced Insuline Resistance.", JBC, 2011, pp. 17467-17477, vol. 286(20).
Pantoliano et al., "High Density Miniaturized Thermal Shift Assays as a General Strategy for Drug Discovery*.", Journal of Biomolecular Screening, 2001, pp. 429-440, vol. 6(6).
Matulis et al., "Thermodynamic Stability of Carbonic Anhydrase: Measurements of Binding Affinity and Stoichiometry Using ThermoFluor.", Biochemistry, 2005, vol. 44, pp. 5258-5266.
Buettner et al., "High-fat diets: modeling the metabolic disorders of human obesity in Rodents.", Obesity, 2007, pp. 798-808, vol. 15.
Van Heek et al., "Diet-induced obese mice develop peripheral, but not central, resistance to lepton.", J Clin Invest, 1997, pp. 385-390, vol. 99.
Winzell, M., "The High-fat Diet-Fed Mouse: A Model for Studying Mechanisms and Treatment of Impaired Glucose Tolerance and Type 2 Diabetes.", Diabetes, Dec. 2004, pp. S215-S219, vol. 53(3).
Barba et al., "Appropriate body-mass index for Asian populations and its implications for policy and intervention strategies.", The Lancet, 2004, pp. 157-162, vol. 363.
International Search Report re: PCT/US2012/057470 dated Dec. 3, 2012.

* cited by examiner

*Primary Examiner* — Paul Zarek
*Assistant Examiner* — George W Kosturko
(74) *Attorney, Agent, or Firm* — Thomas J. Dodd

(57) ABSTRACT

Disclosed are compounds, compositions and methods for treating metabolic diseases, including obesity and diabetes. Such compounds are represented by formula (I) as follows:

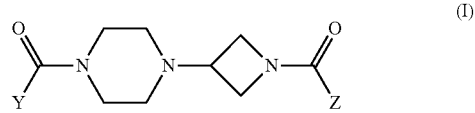

wherein Y and Z are defined herein.

4 Claims, No Drawings

MONOACYLGLYCEROL LIPASE INHIBITORS FOR THE TREATMENT OF METABOLIC DISEASES AND RELATED DISORDERS

CROSS-REFERENCE TO RELATED APPLICATIONS

This application claims priority to U.S. provisional patent application No. 61/541,403, filed Sep. 30, 2011, which is hereby incorporated by reference in its entirety.

STATEMENT REGARDING FEDERALLY SPONSORED RESEARCH OR DEVELOPMENT

The research and development of the invention described below was not federally sponsored.

BACKGROUND OF THE INVENTION

Monoglyceride Lipase (MGL) is a target known in the art and first identified by Wall et al. (*Virus Res.* 1997, 52, 152-167) in 1997 and designated HUKS. Dinh et al. (*Proc. Nat. Acad. Sci.*, 2002, 99, 10819-10824) found that the rat MGL participates in inactivation of 2-arachidonoylglycerol (2-AG), an endogenous cannabinoid monoglyceride. It is highly expressed in regions of rat brain that also express cannabinoid receptors and it appears to assume a presynaptic localization in the hippocampus. Adenovirus-mediated transfer of MGL cDNA into rat cortical neurons increased MGL expression and attenuated 2-AG accumulation induced by N-methyl-D-aspartate/carbachol. MGL inhibitors, on the other hand, have been shown by Schlossburg et al (*Nat. Neurosci.*, 2010, September 13(9), 1113-9) to enhance the signaling of the endocannabinoid system by elevating the level of 2-AG, the endocannabinoid of highest abundance in the central nervous system (CNS) and gastrointestinal tract. For this reason, MGL inhibitors are potentially useful for the treatment of pain, inflammation, and CNS disorders.

In addition to the brain, MGL is expressed in adipocytes, where it functions together with hormone-sensitive lipase (LIPE) to hydrolyze intracellular triglyceride stores, and in the intestine, where it is largely responsible for cleaving monoacyglycerols to form free fatty acids and glycerol. It has been observed by Chon, et al. (*FASEB*, 2008, 22, 807-12) that increased expression of MGL in the intestine causes an obese phenotype, most likely due to hyperphagia (overeating). Further evidence from MGL knockout mice ("MGL-ko mice") (Taschler, et al. *JBC*, 2011, March, published online) showed that MGL-deficiency results in accumulation of 2-AG and other MG species in various tissues, including brain, adipose and liver. Fasted MGL-ko mice exhibited reduced plasma glycerol and triacylglycerol, as well as liver triacylglycerol levels indicative of impaired lipolysis. MGL-ko mice receiving a high-fat diet showed significantly improved glucose tolerance and insulin sensitivity in comparison to wild-type controls. These observations implicate MGL in metabolic diseases and suggest that MGL inhibitors will have beneficial effects on metabolic disorders, including obesity, hyperphagia and diabetes.

It is an object of the present invention to provide MGL inhibitors. It is also an object of the invention to provide a method of treating, ameliorating or preventing metabolic disorders, such as obesity, hyperphagia and diabetes, by the administration of a compound of formula (I). And, it is an object of the invention to provide a pharmaceutical composition comprising a compound of formula (I), useful for treating, ameliorating or preventing metabolic disorders.

SUMMARY OF THE INVENTION

The present invention is directed to a method for treating, ameliorating, or preventing metabolic diseases; comprising, consisting of, and/or consisting essentially of administering to a subject in need thereof, a therapeutically effective amount of a compound of formula (I)

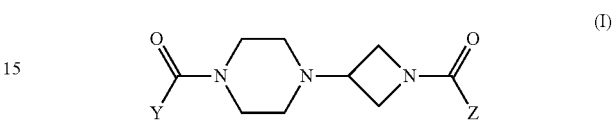

or an enantiomer, diastereomer, solvate, or pharmaceutically acceptable salt thereof;
wherein:
Y is a heteroaryl selected from the group consisting of thienyl, furanyl, thiazolyl, isothiazolyl, oxazolyl, pyridinyl, isoxazolyl, imidazolyl, furazan-3-yl, pyrazolyl, triazolyl, tetrazolyl, and [1,2,3]thiadiazolyl;
wherein Y is optionally independently substituted with one to two substituents selected from the group consisting of fluoro, chloro, bromo, $C_{1-4}$alkyl, cyano, and trifluoromethyl;
Z is a heteroaryl selected from the group consisting of indolyl, indazolyl, benzoxazolyl, benzothiazolyl, benzothienyl, benzofuranyl, imidazo[1,2-a]pyridin-2-yl, pyrrolo[2,3-b]pyridinyl, pyrrolo[3,2-b]pyridinyl, thieno[2,3-b]pyridinyl, quinolinyl, quinazolinyl, and benzimidazolyl;
wherein said Z is optionally independently substituted with one to two substituents selected from the group consisting of $C_{1-4}$alkyl, trifluoromethyl, 2,2,2-trifluoroethoxy-methyl, 2,2,2-trifluoroethoxy, trifluoromethylthio, chloro, fluoro, bromo, and iodo;
with the proviso that a compound of formula (I) is other than a compound wherein Y is thiazol-4-yl and Z is 5-fluoro-3H-benzimidazol-2-yl; a compound wherein Y is thiazol-2-yl and Z is 5-fluoro-1H-benzimidazol-2-yl;
a compound wherein Y is thiazol-4-yl and Z is 5-chloro-benzofuran-2-yl; a compound wherein Y is isothiazol-5-yl and Z is 6-trifluoromethyl-1H-indol-2-yl; a compound wherein Y is thiazol-4-yl and Z is 5-trifluoromethyl-1H-pyrrolo[3,2-b]pyridin-2-yl; a compound wherein Y is thiazol-2-yl and Z is 8-bromo-6-chloro-imidazo[1,2-a]pyridin-2-yl; or a compound wherein Y is thiazol-2-yl and Z is 6-trifluoromethyl-imidazo[1,2-a]pyridin-2-yl.

The present invention is further directed to the use of a compound of formula (I) as herein defined for the preparation of a medicament or a pharmaceutical composition for the treatment, amelioration and/or prevention of metabolic diseases, including obesity and diabetes, in a subject in need thereof.

DETAILED DESCRIPTION OF THE INVENTION

As used herein, the following terms are intended to have the following meanings:

With reference to substituents, the term "independently" refers to the situation that when more than one substituent is possible, the substituents may be the same or different from each other.

The term "alkyl" whether used alone or as part of a substituent group, refers to straight and branched carbon chains having 1 to 8 carbon atoms. Therefore, designated numbers of carbon atoms (e.g., $C_{1-8}$) refer independently to the number of carbon atoms in an alkyl moiety or to the alkyl portion of a larger alkyl-containing substituent. In substituent groups with multiple alkyl groups such as ($C_{1-6}$alkyl)$_2$amino- the $C_{1-6}$alkyl groups of the dialkylamino may be the same or different.

The term "alkoxy" refers to an —O-alkyl group, wherein the term "alkyl" is as defined above.

The terms "alkenyl" and "alkynyl" refer to straight and branched carbon chains having 2 or more carbon atoms, wherein an alkenyl chain contains at least one double bond and an alkynyl chain contains at least one triple bond.

The term "aryl" refers to an unsaturated, aromatic monocyclic or bicyclic ring of 6 to 10 carbon members. Examples of aryl rings include phenyl and naphthalenyl.

The term "heteroaryl" refers to an aromatic monocyclic or bicyclic aromatic ring system having 5 to 10 ring members and which contains carbon atoms and from 1 to 4 heteroatoms independently selected from the group consisting of N, O, and S. Included within the term heteroaryl are aromatic rings of 5 or 6 members, wherein the ring consists of carbon atoms and has at least one heteroatom member. Suitable heteroatoms include nitrogen, oxygen, and sulfur. In the case of 5 membered rings, the heteroaryl ring preferably contains one member of nitrogen, oxygen, or sulfur and, in addition, up to 3 additional nitrogens. In the case of 6 membered rings, the heteroaryl ring preferably contains from 1 to 3 nitrogen atoms. For the case wherein the 6 membered ring has 3 nitrogens, at most 2 nitrogen atoms are adjacent. When a heteroaryl is bicyclic, at least one heteroatom is present in at least one ring. Examples of heteroaryl groups include furyl, thienyl, pyrrolyl, oxazolyl, thiazolyl, imidazolyl, pyrazolyl, isoxazolyl, isothiazolyl, oxadiazolyl, triazolyl, thiadiazolyl, pyridinyl, pyridazinyl, pyrimidinyl and pyrazinyl. Unless otherwise noted, the heteroaryl is attached to its pendant group at any heteroatom or carbon atom that results in a stable structure.

The term "halogen" or "halo" refers to fluorine, chlorine, bromine and iodine.

The term "oxo" refers to the group (=O).

Whenever the term "alkyl" or "aryl" or either of their prefix roots appear in a name of a substituent (e.g., arylalkyl, alkylamino) the name is to be interpreted as including those limitations given above for "alkyl" and "aryl." Designated numbers of carbon atoms (e.g., $C_1$-$C_6$) refer independently to the number of carbon atoms in an alkyl moiety, an aryl moiety, or in the alkyl portion of a larger substituent in which alkyl appears as its prefix root. For alkyl and alkoxy substituents, the designated number of carbon atoms includes all of the independent members included within a given range specified. For example $C_{1-6}$ alkyl would include methyl, ethyl, propyl, butyl, pentyl and hexyl individually as well as sub-combinations thereof (e.g., $C_{1-2}$, $C_{1-3}$, $C_{1-4}$, $C_{1-5}$, $C_{2-6}$, $C_{3-6}$, $C_{4-6}$, $C_{5-6}$, $C_{2-5}$, etc.).

In general, under standard nomenclature rules used throughout this disclosure, the terminal portion of the designated side chain is described first followed by the adjacent functionality toward the point of attachment. Thus, for example, a "$C_1$-$C_6$ alkylcarbonyl" substituent refers to a group of the formula:

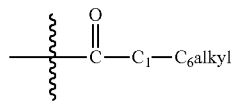

The term "R" at a stereocenter designates that the stereocenter is purely of the R-configuration as defined in the art; likewise, the term "S" means that the stereocenter is purely of the S-configuration. As used herein, the terms "*R" or "*S" at a stereocenter are used to designate that the stereocenter is of pure but unknown configuration. As used herein, the term "RS" refers to a stereocenter that exists as a mixture of the R- and S-configurations. Similarly, the terms "*RS" or "*SR" refer to a stereocenter that exists as a mixture of the R- and S-configurations and is of unknown configuration relative to another stereocenter within the molecule.

Compounds containing one stereocenter drawn without a stereo bond designation are a mixture of 2 enantiomers. Compounds containing 2 stereocenters both drawn without stereo bond designations are a mixture of 4 diastereomers. Compounds with 2 stereocenters both labeled "RS" and drawn with stereo bond designations are a 2-component mixture with relative stereochemistry as drawn. Compounds with 2 stereocenters both labeled "*RS" and drawn with stereo bond designations are a 2-component mixture with relative stereochemistry unknown. Unlabeled stereocenters drawn without stereo bond designations are a mixture of the R- and S-configurations. For unlabeled stereocenters drawn with stereo bond designations, the absolute stereochemistry is as depicted.

Unless otherwise noted, it is intended that the definition of any substituent or variable at a particular location in a molecule be independent of its definitions elsewhere in that molecule. It is understood that substituents and substitution patterns on the compounds of formula (I) can be selected by one of ordinary skill in the art to provide compounds that are chemically stable and that can be readily synthesized by techniques known in the art as well as those methods set forth herein.

The term "subject" as used herein, refers to an animal, preferably a mammal, most preferably a human, who has been the object of treatment, observation, or experiment.

The term "therapeutically effective amount" as used herein, means that amount of active compound or pharmaceutical agent that elicits the biological or medicinal response in a tissue system, animal or human that is being sought by a researcher, veterinarian, medical doctor or other clinician, which includes alleviation of the symptoms of the disease or disorder being treated.

The term "composition" is intended to encompass a product comprising the specified ingredients in therapeutically effective amounts, as well as any product that results, directly or indirectly, from combinations of the specified ingredients in the specified amounts.

As used herein, unless otherwise noted, the terms "treating", "treatment", "ameliorating" and the like, shall include the management and care of a subject or patient (preferably mammal, more preferably human) for the purpose of combating a disease, condition, or disorder and includes the administration of a compound of the present invention to prevent the onset of the symptoms or complications, alleviate the symptoms or complications, or eliminate the disease, condition, syndrome, or disorder.

As used herein, unless otherwise noted, the terms "preventing" and "prevention" shall include (a) reduction in the frequency of one or more symptoms; (b) reduction in the severity of one or more symptoms; (c) the delay or avoidance of the development of additional symptoms; and/or (d) delay or avoidance of the development of the disease, disorder, syndrome, or condition.

One skilled in the art will recognize that where the present invention is directed to methods of prevention, a subject in need of thereof (i.e., a subject in need of prevention) includes any subject (preferably a mammal, more preferably a human) who has experienced or exhibited at least one symptom of the disorder, disease, syndrome, or condition to be prevented. Further, a subject in need thereof may additionally be a subject (preferably a mammal, more preferably a human) who has not exhibited any symptoms of the disorder, disease, syndrome, or condition to be prevented, but who has been deemed by a physician, clinician, or other medical professional to be at risk of developing said disorder, disease, syndrome, or condition. For example, the subject may be deemed at risk of developing a disorder, disease, syndrome, or condition (and therefore in need of prevention or preventive treatment) as a consequence of the subject's medical history, including, but not limited to, family history, pre-disposition, co-existing (comorbid) disorders or conditions, genetic testing, and the like.

The term "MGL inhibitor" is intended to encompass a compound that interacts with MGL to substantially reduce or eliminate its catalytic activity, thereby increasing the concentrations of its substrate(s). The term "MGL-modulated" is used to refer to the condition of being affected by the modulation of the MGL enzyme including the condition of being affected by the inhibition of the MGL enzyme, such as, for example, metabolic diseases including obesity and diabetes As used herein, unless otherwise noted, the term "affect" or "affected" (when referring to a disease, syndrome, condition or disorder that is affected by inhibition of MGL) implies a reduction in the frequency and/or severity of one or more symptoms or manifestations of said disease, syndrome, condition or disorder; and/or imply the prevention of the development of one or more symptoms or manifestations of said disease, syndrome, condition or disorder or the development of the disease, condition, syndrome or disorder.

Compounds of formula (I) are useful in methods for treating, ameliorating and/or preventing metabolic diseases or a disorder that causes such diseases by the inhibition of MGL. Such methods comprise, consist of and/or consist essentially of administering to a subject, including an animal, a mammal, and a human in need of such treatment, amelioration and/or prevention, a therapeutically effective amount of a compound of formula (I) or a solvate or pharmaceutically acceptable salt thereof. More particularly, a compound of formula (I) is useful for treating, ameliorating and/or preventing metabolic diseases, such as obesity, hyperphagia, and diabetes, comprising administering to a subject in need thereof a therapeutically effective amount of a compound of formula (I), as herein defined.

Examples of metabolic disorder, syndrome, diseases or conditions include, but are not limited to, diabetes, hyperphagia, overweight, obesity, obesity-associated insulin resistance, atherosclerosis, and associated symptoms or complications thereof. They also include such conditions as IDDM (insulin-dependent diabetes mellitus), NIDDM (non insulin-dependent diabetes mellitus), IGT (Impaired Glucose Tolerance), IFG (Impaired Fasting Glucose), Syndrome X (i.e., Metabolic Syndrome), hyperglycemia, elevated blood glucose level, and insulin resistance. "Prediabetic condition" or "prediabetic state" include IGT and IFG.

The term "obesity" refers to a condition in which there is an excess of body fat. The operational definition of obesity is often based on the Body Mass Index (BMI), which is calculated as body weight per height in meters squared ($kg/m^2$). An "obese subject" is an otherwise healthy subject with a Body Mass Index (BMI) greater than or equal to 30 kg/m2 or a subject having at least one co-morbidity with a BMI greater than or equal to 27 $kg/m^2$. A "subject at risk of obesity" is an otherwise healthy subject with a BMI of 25 $kg/m^2$ to less than 30 $kg/m^2$ or a subject having at least one co-morbidity with a BMI of 25 $kg/m^2$ to less than 27 $kg/m^2$.

The increased risks associated with obesity occur at a lower BMI in Asian populations (Barba, et al. *The Lancet*, 2004, 363, 157-162). In Asian countries, the available data do not indicate one clear BMI cut-off point for all populations for overweight or obesity individuals. In Japan, "obesity" refers to a condition whereby a subject with at least one obesity-induced or obesity-related co-morbidity, that requires weight reduction or that would be improved by weight reduction, has a BMI greater than or equal to 25 kg/m2. As another example in Asia-Pacific Island populations such as Indonesia and Singapore, a "subject at risk of obesity" is a subject with a BMI of greater than 23 $kg/m^2$ to less than 25 $kg/m^2$.

As used herein, the term "obesity" is meant to encompass all of the above definitions of obesity.

Obesity-induced or obesity-related co-morbidities include, but are not limited to, diabetes, impaired glucose tolerance, insulin resistance syndrome, dyslipidemia, hypertension, hyperuricacidemia, gout, coronary artery disease, myocardial infarction, angina pectoris, sleep apnea syndrome, Pickwickian syndrome, fatty liver; cerebral infarction, cerebral thrombosis, transient ischemic attack, orthopedic disorders, arthritis deformans, lumbodynia, emmeniopathy, and infertility. In particular, co-morbidities include: hypertension, hyperlipidemia, dyslipidemia, glucose intolerance, cardiovascular disease, sleep apnea, diabetes mellitus, and other obesity-related conditions.

Treatment of obesity and obesity-related disorders, diseases, syndromes, and conditions refer to the administration of at least one compound of the present invention for the reduction of or maintenance of the body weight of an obese subject.

In an embodiment, the present invention is directed to a method for treating, ameliorating, or preventing metabolic disorders, diseases, syndromes, and conditions; comprising, consisting of, and/or consisting essentially of administering to a subject in need thereof, a therapeutically effective amount of a compound of formula (I)

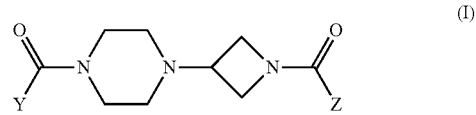

or an enantiomer, diastereomer, solvate, or pharmaceutically acceptable salt thereof;
wherein:
a) Y is a heteroaryl selected from the group consisting of thienyl, furanyl, thiazolyl, isothiazolyl, oxazolyl, pyridinyl, and [1,2,3]thiadiazolyl;
  wherein Y is optionally substituted with one to two substituents independently selected from the group consisting of fluoro, chloro, bromo, and trifluoromethyl;

b) Y is a heteroaryl selected from the group consisting of thienyl, furanyl, thiazolyl, isothiazolyl, pyridinyl, and [1,2,3]thiadiazolyl;
   wherein Y is optionally substituted with one to two substituents independently selected from the group consisting of fluoro, chloro, bromo, and trifluoromethyl;
c) Y is a heteroaryl selected from the group consisting of thienyl, furanyl, thiazolyl, and isothiazolyl;
   wherein Y is optionally substituted with one to two substituents independently selected from the group consisting of fluoro, chloro, bromo, and trifluoromethyl;
d) Z is a heteroaryl selected from the group consisting of indolyl, benzoxazolyl, benzothiazolyl, benzothienyl, benzofuranyl, pyrrolo[2,3-b]pyridinyl, thieno[2,3-b]pyridinyl, quinolinyl, and benzimidazolyl;
   wherein Z is optionally independently substituted with one to two substituents selected from the group consisting of $C_{1-4}$alkyl, trifluoromethyl, 2,2,2-trifluoroethoxy-methyl, 2,2,2-trifluoroethoxy, trifluoromethylthio, chloro, fluoro, bromo, and iodo;
e) Z is a heteroaryl selected from the group consisting of indolyl, benzothiazolyl, benzothienyl, benzofuranyl, pyrrolo[2,3-b]pyridinyl, thieno[2,3-b]pyridinyl, quinolinyl, and benzimidazolyl;
   wherein Z is optionally independently substituted with one to two substituents selected from the group consisting of $C_{1-4}$alkyl, trifluoromethyl, 2,2,2-trifluoroethoxy-methyl, 2,2,2-trifluoroethoxy, chloro, fluoro, bromo, and iodo;
f) Z is a heteroaryl selected from the group consisting of indolyl, benzothiazolyl, benzothienyl, pyrrolo[2,3-b]pyridinyl, and thieno[2,3-b]pyridinyl;
   wherein Z is optionally independently substituted with one to two substituents selected from the group consisting of $C_{1-4}$alkyl, trifluoromethyl, 2,2,2-trifluoroethoxy-methyl, 2,2,2-trifluoroethoxy, chloro, fluoro, bromo, and iodo;
and combinations of a) through f) above;
with the proviso that a compound of formula (I) is other than
   a compound wherein Y is thiazol-4-yl and Z is 5-fluoro-3H-benzimidazol-2-yl; a compound wherein Y is thiazol-2-yl and Z is 5-fluoro-1H-benzimidazol-2-yl;
   a compound wherein Y is thiazol-4-yl and Z is 5-chloro-benzofuran-2-yl; a compound wherein Y is isothiazol-5-yl and Z is 6-trifluoromethyl-1H-indol-2-yl; a compound wherein Y is thiazol-4-yl and Z is 5-trifluoromethyl-1H-pyrrolo[3,2-b]pyridin-2-yl; a compound wherein Y is thiazol-2-yl and Z is 8-bromo-6-chloro-imidazo[1,2-a]pyridin-2-yl; a compound wherein Y is thiazol-2-yl and Z is 6-trifluoromethyl-imidazo[1,2-a]pyridin-2-yl.

In an embodiment, the present invention is directed to a method for treating, ameliorating, or preventing metabolic disorders, diseases, syndromes, and conditions; comprising, consisting of, and/or consisting essentially of administering to a subject in need thereof, a therapeutically effective amount of a compound of formula (I)

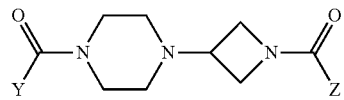

(I)

or an enantiomer, diastereomer, solvate, or pharmaceutically acceptable salt thereof;
wherein:
   Y is a heteroaryl selected from the group consisting of thienyl, furanyl, thiazolyl, isothiazolyl, oxazolyl, pyridinyl, and [1,2,3]thiadiazolyl;
   wherein Y is optionally substituted with one to two substituents independently selected from the group consisting of fluoro, chloro, bromo, and trifluoromethyl; and
   Z is a heteroaryl selected from the group consisting of indolyl, benzoxazolyl, benzothiazolyl, benzothienyl, benzofuranyl, pyrrolo[2,3-b]pyridinyl, thieno[2,3-b]pyridinyl, quinolinyl, and benzimidazolyl;
   wherein Z is optionally independently substituted with one to two substituents selected from the group consisting of $C_{1-4}$alkyl, trifluoromethyl, 2,2,2-trifluoroethoxy-methyl, 2,2,2-trifluoroethoxy, trifluoromethylthio, chloro, fluoro, bromo, and iodo;
with the proviso that a compound of formula (I) is other than
   a compound wherein Y is thiazol-4-yl and Z is 5-fluoro-3H-benzimidazol-2-yl; a compound wherein Y is thiazol-2-yl and Z is 5-fluoro-1H-benzimidazol-2-yl;
   a compound wherein Y is thiazol-4-yl and Z is 5-chloro-benzofuran-2-yl; or a compound wherein Y is isothiazol-5-yl and Z is 6-trifluoromethyl-1H-indol-2-yl.

In an embodiment, the present invention is directed to a method for treating, ameliorating, or preventing metabolic disorders, diseases, syndromes, and conditions; comprising, consisting of, and/or consisting essentially of administering to a subject in need thereof, a therapeutically effective amount of a compound of formula (I)

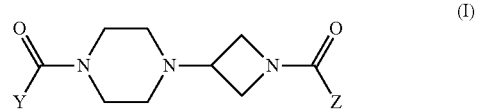

(I)

or an enantiomer, diastereomer, solvate, or pharmaceutically acceptable salt thereof;
wherein:
   Y is a heteroaryl selected from the group consisting of thienyl, furanyl, thiazolyl, isothiazolyl, pyridinyl, and [1,2,3]thiadiazolyl;
   wherein Y is optionally substituted with one to two substituents independently selected from the group consisting of fluoro, chloro, bromo, and trifluoromethyl; and
   Z is a heteroaryl selected from the group consisting of indolyl, benzothiazolyl, benzothienyl, benzofuranyl, pyrrolo[2,3-b]pyridinyl, thieno[2,3-b]pyridinyl, quinolinyl, and benzimidazolyl;
   wherein Z is optionally independently substituted with one to two substituents selected from the group consisting of $C_{1-4}$alkyl, trifluoromethyl, 2,2,2-trifluoroethoxy-methyl, 2,2,2-trifluoroethoxy, chloro, fluoro, bromo, and iodo;
with the proviso that a compound of formula (I) is other than
   a compound wherein Y is thiazol-4-yl and Z is 5-fluoro-3H-benzimidazol-2-yl; a compound wherein Y is thiazol-2-yl and Z is 5-fluoro-1H-benzimidazol-2-yl;
   a compound wherein Y is thiazol-4-yl and Z is 5-chloro-benzofuran-2-yl; or a compound wherein Y is isothiazol-5-yl and Z is 6-trifluoromethyl-1H-indol-2-yl.

In an embodiment, the present invention is directed to a method for treating, ameliorating, or preventing metabolic disorders, diseases, syndromes, and conditions; comprising, consisting of, and/or consisting essentially of administering to a subject in need thereof, a therapeutically effective amount of a compound of formula (I)

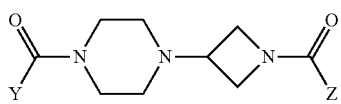

or an enantiomer, diastereomer, solvate, or pharmaceutically acceptable salt thereof;
wherein:
Y is a heteroaryl selected from the group consisting of thienyl, furanyl, thiazolyl, and isothiazolyl;
wherein Y is optionally substituted with one to two substituents independently selected from the group consisting of fluoro, chloro, bromo, and trifluoromethyl;
Z is a heteroaryl selected from the group consisting of indolyl, benzothiazolyl, benzothienyl, pyrrolo[2,3-b]pyridinyl, and thieno[2,3-b]pyridinyl;
wherein Z is optionally independently substituted with one to two substituents selected from the group consisting of $C_{1-4}$alkyl, trifluoromethyl, 2,2,2-trifluoroethoxy-methyl, 2,2,2-trifluoroethoxy, chloro, fluoro, bromo, and iodo;
with the proviso that a compound of formula (I) is other than
a compound wherein Y is isothiazol-5-yl and Z is 6-trifluoromethyl-1H-indol-2-yl.

An embodiment of the present invention is directed to a method for treating, ameliorating, or preventing metabolic disorders, diseases, syndromes, and conditions, including obesity and diabetes; comprising, consisting of, and/or consisting essentially of administering to a subject in need thereof, a therapeutically effective amount of 1-(1-{[3-Chloro-6-(trifluoromethyl)-1-benzothiophen-2-yl]carbonyl}azetidin-3-yl)-4-(1,3-thiazol-4-ylcarbonyl)piperazine (Compound 1);

Compound 1

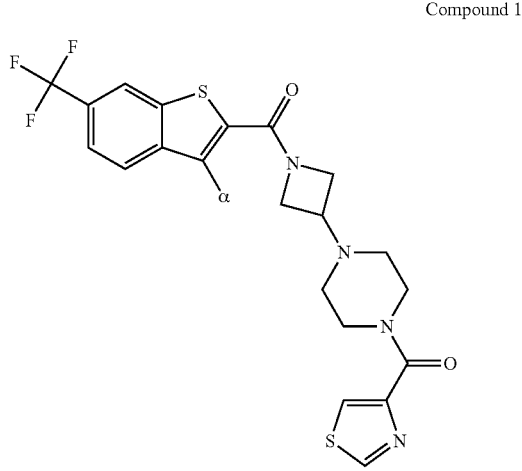

or a solvate or pharmaceutically acceptable salt thereof.

For use in medicine, salts of a compound of formula (I) refer to non-toxic "pharmaceutically acceptable salts." Other salts may, however, be useful in the preparation of a compound of formula (I) or of its pharmaceutically acceptable salts thereof. Suitable pharmaceutically acceptable salts of a compound of formula (I) include acid addition salts which can, for example, be formed by mixing a solution of the compound with a solution of a pharmaceutically acceptable acid such as hydrochloric acid, sulfuric acid, fumaric acid, maleic acid, succinic acid, acetic acid, benzoic acid, citric acid, tartaric acid, carbonic acid or phosphoric acid. Furthermore, where a compound of formula (I) carries an acidic moiety, suitable pharmaceutically acceptable salts thereof may include alkali metal salts, such as sodium or potassium salts; alkaline earth metal salts, such as calcium or magnesium salts; and salts formed with suitable organic ligands, such as quaternary ammonium salts. Thus, representative pharmaceutically acceptable salts include acetate, benzenesulfonate, benzoate, bicarbonate, bisulfate, bitartrate, borate, bromide, calcium edetate, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isothionate, lactate, lactobionate, laurate, malate, maleate, mandelate, mesylate, methylbromide, methylnitrate, methylsulfate, mucate, napsylate, nitrate, N-methylglucamine ammonium salt, oleate, pamoate (embonate), palmitate, pantothenate, phosphate/diphosphate, polygalacturonate, salicylate, stearate, sulfate, subacetate, succinate, tannate, tartrate, teoclate, tosylate, triethiodide and valerate.

Representative acids and bases that may be used in the preparation of pharmaceutically acceptable salts include acids including acetic acid, 2,2-dichloroacetic acid, acylated amino acids, adipic acid, alginic acid, ascorbic acid, L-aspartic acid, benzenesulfonic acid, benzoic acid, 4-acetamidobenzoic acid, (+)-camphoric acid, camphorsulfonic acid, (+)-(1S)-camphor-10-sulfonic acid, capric acid, caproic acid, caprylic acid, cinnamic acid, citric acid, cyclamic acid, dodecylsulfuric acid, ethane-1,2-disulfonic acid, ethanesulfonic acid, 2-hydroxy-ethanesulfonic acid, formic acid, fumaric acid, galactaric acid, gentisic acid, glucoheptonic acid, D-gluconic acid, D-glucoronic acid, L-glutamic acid, α-oxoglutaric acid, glycolic acid, hippuric acid, hydrobromic acid, hydrochloric acid, (+)-L-lactic acid, (±)-DL-lactic acid, lactobionic acid, maleic acid, (−)-L-malic acid, malonic acid, (±)-DL-mandelic acid, methanesulfonic acid, naphthalene-2-sulfonic acid, naphthalene-1,5-disulfonic acid, 1-hydroxy-2-naphthoic acid, nicotinic acid, nitric acid, oleic acid, orotic acid, oxalic acid, palmitic acid, pamoic acid, phosphoric acid, L-pyroglutamic acid, salicylic acid, 4-amino-salicylic acid, sebaic acid, stearic acid, succinic acid, sulfuric acid, tannic acid, (+)-L-tartaric acid, thiocyanic acid, p-toluenesulfonic acid and undecylenic acid; and bases including ammonia, L-arginine, benethamine, benzathine, calcium hydroxide, choline, deanol, diethanolamine, diethylamine, 2-(diethylamino)-ethanol, ethanolamine, ethylenediamine, N-methylglucamine, hydrabamine, 1H-imidazole, L-lysine, magnesium hydroxide, 4-(2-hydroxyethyl)-morpholine, piperazine, potassium hydroxide, 1-(2-hydroxyethyl)-pyrrolidine, sodium hydroxide, triethanolamine, tromethamine and zinc hydroxide.

Embodiments of the present invention include prodrugs of a compound of formula (I). In general, such prodrugs will be functional derivatives of the compounds that are readily convertible in vivo into the required compound. Thus, in the methods of treating or preventing embodiments of the present invention, the term "administering" encompasses the treatment or prevention of the various diseases, conditions, syndromes and disorders described with the compound specifically disclosed or with a compound that may not be specifically disclosed, but which converts to the specified compound in vivo after administration to a patient. Conventional procedures for the selection and preparation of suitable prodrug derivatives are described, for example, in "Design of Prodrugs", ed. H. Bundgaard, Elsevier, 1985.

Some of the crystalline forms for a compound of formula (I) may exist as polymorphs and as such are intended to be included in the present invention. In addition, some of the compounds may form solvates with water (i.e., hydrates) or common organic solvents, and such solvates are also intended to be encompassed within the scope of this invention. The skilled artisan will understand that the term compound as used herein, is meant to include solvated compounds of formula (I).

During any of the processes for preparation of a compound of formula (I) of the various embodiments of the present invention, it may be necessary and/or desirable to protect sensitive or reactive groups on any of the molecules concerned. This may be achieved by means of conventional protecting groups, such as those described in *Protective Groups in Organic Chemistry, Second Edition*, J. F. W. McOmie, Plenum Press, 1973; T. W. Greene & P. G. M. Wuts, *Protective Groups in Organic Synthesis*, John Wiley & Sons, 1991; and T. W. Greene & P. G. M. Wuts, *Protective Groups in Organic Synthesis, Third Edition*, John Wiley & Sons, 1999. The protecting groups may be removed at a convenient subsequent stage using methods known from the art.

Even though a compound of formula (I) and the embodiments of the present invention (including their pharmaceutically acceptable salts and pharmaceutically acceptable solvates) can be administered alone, they will generally be administered in admixture with a pharmaceutically acceptable carrier, a pharmaceutically acceptable excipient and/or a pharmaceutically acceptable diluent selected with regard to the intended route of administration and standard pharmaceutical or veterinary practice. Thus, particular embodiments of the present invention are directed to pharmaceutical and veterinary compositions comprising a compound of formula (I) and at least one pharmaceutically acceptable carrier, pharmaceutically acceptable excipient, and/or pharmaceutically acceptable diluent.

By way of example, in the pharmaceutical compositions of embodiments of the present invention, a compound of formula (I) may be admixed with any suitable binder(s), lubricant(s), suspending agent(s), coating agent(s), solubilizing agent(s), and combinations thereof.

Solid oral dosage forms, such as tablets or capsules, containing the compounds of the present invention may be administered in at least one dosage form at a time, as appropriate. It is also possible to administer the compounds in sustained release formulations.

Additional oral forms in which the present inventive compounds may be administered include elixirs, solutions, syrups, and suspensions; each optionally containing flavoring agents and coloring agents.

Alternatively, a compound of formula (I) can be administered by inhalation (intratracheal or intranasal) or in the form of a suppository or pessary, or it may be applied topically in the form of a lotion, solution, cream, ointment or dusting powder. For example, it can be incorporated into a cream comprising, consisting of, and/or consisting essentially of an aqueous emulsion of polyethylene glycols or liquid paraffin. It can also be incorporated, at a concentration of between about 1% and about 10% by weight of the cream, into an ointment comprising, consisting of, and/or consisting essentially of a white wax or white soft paraffin base together with any stabilizers and preservatives as may be required. An alternative means of administration includes transdermal administration by using a skin or transdermal patch.

The pharmaceutical compositions of the present invention (as well as a compound of formula (I) alone) can also be injected parenterally, for example intracavernosally, intravenously, intramuscularly, subcutaneously, intradermally or intrathecally. In this case, the compositions will also include at least one of a suitable carrier, a suitable excipient, and a suitable diluent.

For parenteral administration, the pharmaceutical compositions of the present invention are best used in the form of a sterile aqueous solution that may contain other substances, for example, enough salts and monosaccharides to make the solution isotonic with blood.

For buccal or sublingual administration, the pharmaceutical compositions of the present invention may be administered in the form of tablets or lozenges, which can be formulated in a conventional manner.

By way of further example, pharmaceutical compositions containing a compound of formula (I) as the active ingredient can be prepared by mixing a compound of formula (I) with a pharmaceutically acceptable carrier, a pharmaceutically acceptable diluent, and/or a pharmaceutically acceptable excipient according to conventional pharmaceutical compounding techniques. The carrier, excipient, and diluent may take a wide variety of forms depending upon the desired route of administration (e.g., oral, parenteral, etc.). Thus for liquid oral preparations, such as suspensions, syrups, elixirs and solutions, suitable carriers, excipients and diluents include water, glycols, oils, alcohols, flavoring agents, preservatives, stabilizers, coloring agents and the like; for solid oral preparations, such as powders, capsules and tablets, suitable carriers, excipients and diluents include starches, sugars, diluents, granulating agents, lubricants, binders, disintegrating agents and the like. Solid oral preparations also may be optionally coated with substances, such as, sugars, or be enterically-coated so as to modulate the major site of absorption and disintegration. For parenteral administration, the carrier, excipient and diluent will usually include sterile water, and other ingredients may be added to increase solubility and preservation of the composition. Injectable suspensions or solutions may also be prepared utilizing aqueous carriers along with appropriate additives, such as solubilizers and preservatives.

A therapeutically effective amount of a compound of formula (I) or a pharmaceutical composition thereof includes a dose range from about 0.1 mg to about 3000 mg, or any particular amount or range therein, in particular from about 1 mg to about 1000 mg, or any particular amount or range therein, or, more particularly, from about 10 mg to about 500 mg, or any particular amount or range therein, of active ingredient in a regimen of about 1 to about 4 times per day for an average (70 kg) human; although, it is apparent to one skilled in the art that the therapeutically effective amount for a compound of formula (I) will vary as will the diseases, syndromes, conditions, and disorders being treated.

For oral administration, a pharmaceutical composition is preferably provided in the form of tablets containing about 0.01, about 10, about 50, about 100, about 150, about 200, about 250, and about 500 milligrams of a compound of formula (I).

Advantageously, a compound of formula (I) may be administered in a single daily dose, or the total daily dosage may be administered in divided doses of two, three and four times daily.

Optimal dosages of a compound of formula (I) to be administered may be readily determined and will vary with the particular compound used, the mode of administration, the strength of the preparation and the advancement of the disease, syndrome, condition or disorder. In addition, factors associated with the particular subject being treated, including subject gender, age, weight, diet and time of administration, will result in the need to adjust the dose to achieve an appropriate therapeutic level and desired therapeutic effect. The above dosages are thus exemplary of the average case. There can be, of course, individual instances wherein higher or lower dosage ranges are merited, and such are within the scope of this invention.

A compound of formula (I) may be administered in any of the foregoing compositions and dosage regimens or by means of those compositions and dosage regimens established in the art whenever use of a compound of formula (I) is required for a subject in need thereof.

As an MGL inhibitor, a compound of formula (I) is useful in methods for treating and preventing a disease, a syndrome, a condition or a disorder in a subject, including an animal, a mammal and a human in which the disease, the syndrome, the condition or the disorder is affected by the modulation of the MGL enzyme. Such methods comprise, consist of and/or consist essentially of administering to a subject, including an animal, a mammal, and a human in need of such treatment or prevention a therapeutically effective amount of a compound of formula (I). In particular, a compound of formula (I) is useful for preventing or treating metabolic diseases, including obesity and diabetes.

General Synthetic Methods

Representative compounds of the present invention can be synthesized in accordance with the general synthetic methods described below and illustrated in the schemes and examples that follow. Since the schemes are an illustration, the invention should not be construed as being limited by the chemical reactions and conditions described in the schemes. The various starting materials used in the schemes and examples are commercially available or may be prepared by methods well within the skill of persons versed in the art. The variables are as defined herein.

Abbreviations used in the instant specification, particularly the schemes and examples, are as follows:
CAN eerie ammonium nitrate
DCC N,N'-dicyclohexyl-carbodiimide
DCE 1,2-dichloroethane
DCM dichloromethane
DIAD diisopropyl azodicarboxylate
DIPEA diisopropyl-ethyl amine
DMF N,N-dimethylformamide
DMSO dimethylsulfoxide
DPPA diphenylphosphoryl azide
EDC N-(3-dimethylaminopropyl)-N'-ethylcarbodiimide hydrochloride
ESI electrospray ionization
EtOAc ethyl acetate
EtOH ethanol
HATU O-(1H-7-azabenzotriazol-1-yl)-1,1,3,3-tetramethyluronium hexafluorophosphate
HBTU O-(1H-benzotriazol-1-yl)-1,1,3,3-tetramethyluronium hexafluorophosphate
HEK human embryonic kidney
HPLC high performance liquid chromatography
mCPBA meta-chloroperoxybenzoic acid
MeCN acetonitrile
MeOH methanol
MeOTf methyl triflate
MHz megahertz
min minutes
MS mass spectrometry
NBS N-bromosuccinimide
NMR nuclear magnetic resonance
PyBrOP bromo-tris-pyrrolidinophosphonium hexafluorophosphate
RP reverse-phase
$R_t$ retention time
TEA/Et$_3$N triethylamine
TFA trifluoroacetic acid
THF tetrahydrofuran
TLC thin layer chromatography
TMS tetramethylsilane Scheme A illustrates a route for the synthesis compounds of formula (I), wherein Y and Z are as defined herein.

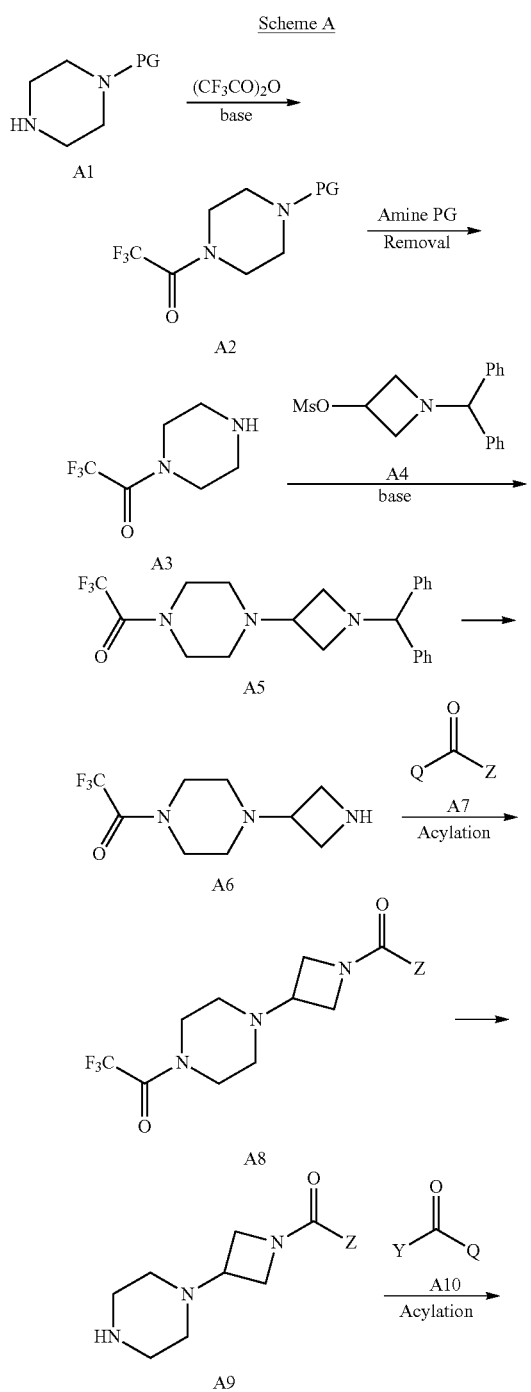

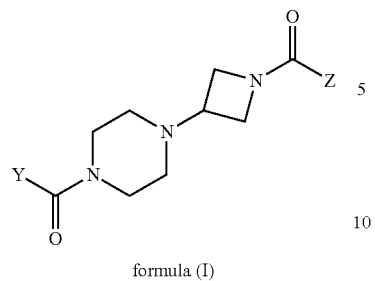

formula (I)

A compound of formula A1 wherein PG is a conventional amino protecting group such as Boc, Fmoc, Cbz, and the like, is either commercially available or may be prepared by known methods described in the scientific literature. A compound of formula A1, in the presence of a non-nucleophilic base such as pyridine, may be treated with trifluoroacetic anhydride to afford a compound of formula A2. Removal of the protecting group (PG) by conventional methods affords a compound of formula A3. A compound of formula A3 may be treated with a compound of formula A4 in the presence of a hindered amine base such as DIPEA to afford a compound of formula A5. Treatment of a compound of formula A5 with 1-chloroethyl chloroformate followed by methanolysis affords the corresponding amine of formula A6. A compound of formula A6 may be coupled with a carboxylic acid of formula A7 wherein Q is hydroxy, in the presence of an appropriate coupling agent such as HATU, DCC, EDC, HBTU, PyBrOP, and the like; optionally in the presence of a base such as DIPEA, to afford an amide of formula A8. Similarly, an acid chloride of formula A7 wherein Q is chloro may be used to effect the acylation of a compound of formula A6. In such case a non-nucleophilic base such as pyridine may be added to afford an amide of formula A8. Removal of the trifluoroacetyl group of a compound of formula A8 may be accomplished by the action of potassium carbonate or TEA in the presence of an alcoholic solvent such as methanol to afford a compound of formula A9. A compound of formula A9 may be acylated with a carboxylic acid or acid chloride of formula A10, wherein Q is hydroxy or chloride, respectively. Appropriate coupling conditions when using a compound of formula A10 (wherein Q is OH) include a coupling agent such as HATU, DCC, EDC, HBTU, PyBrOP, and the like; and a base such as DIPEA to afford a compound of formula (I)-A. When the acylation is effected by the addition of the corresponding acid chloride, the addition of a non-nucleophilic base such as pyridine affords a compound of formula (I).

Scheme B illustrates an alternate route for the synthesis compounds of formula (I), wherein Y and Z are as defined herein.

Scheme B

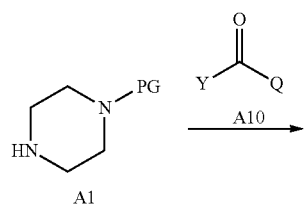

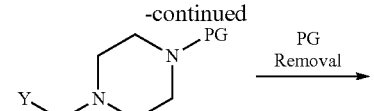

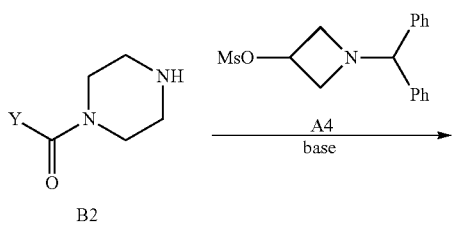

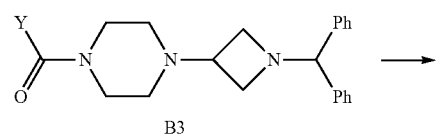

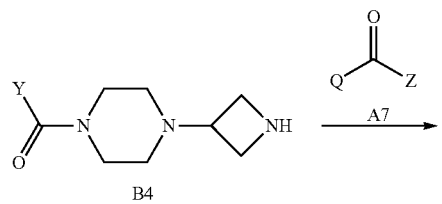

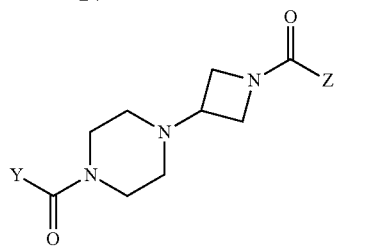

formula (I)

A compound of formula A1 may be acylated with a compound of formula A10 using methods and reagents previously described in Scheme A to afford a compound of formula B1. Upon conventional removal of protecting group PG, a compound of formula B2 may be treated with a compound of formula A4 in the presence of a hindered amine base such as DIPEA using the methods described in Scheme A to afford a compound of formula B3. Treatment of a compound of formula B3 with 1-chloroethyl chloroformate followed by methanolysis affords the corresponding amine of formula B4. An acylation reaction with a compound of formula A7 using the methods described in Scheme A affords the corresponding compound of formula (I)-A.

Scheme C illustrates an alternate route for the synthesis compounds of formula (I), wherein Y and Z are as defined herein.

Scheme C

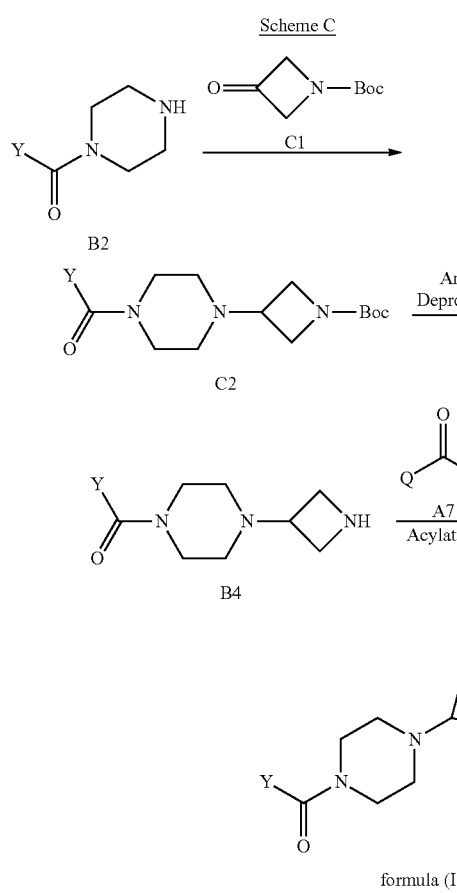

A compound of formula B2 may be treated with a ketone of formula C1 in the presence of decaborane or a reducing agent, such as, sodium triacetoxyborohydride, to afford a compound of formula C2. Removal of the Boc-amino protecting group, using conventional reagents and methods, affords a compound of formula B4. Coupling with a compound of formula A7 as described herein provides a compound of formula (I)-A.

Scheme D illustrates a route for the synthesis compounds of formula (I)-D, wherein Y and Z are as defined herein.

Scheme D

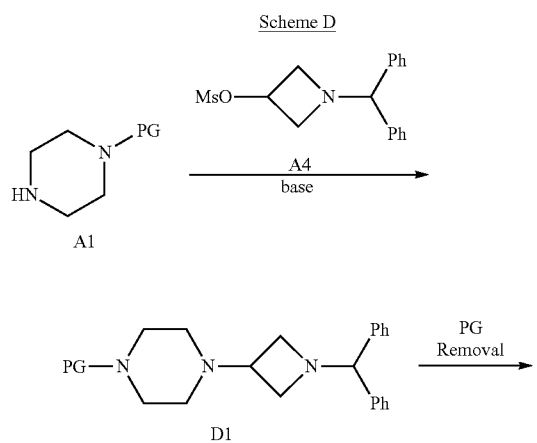

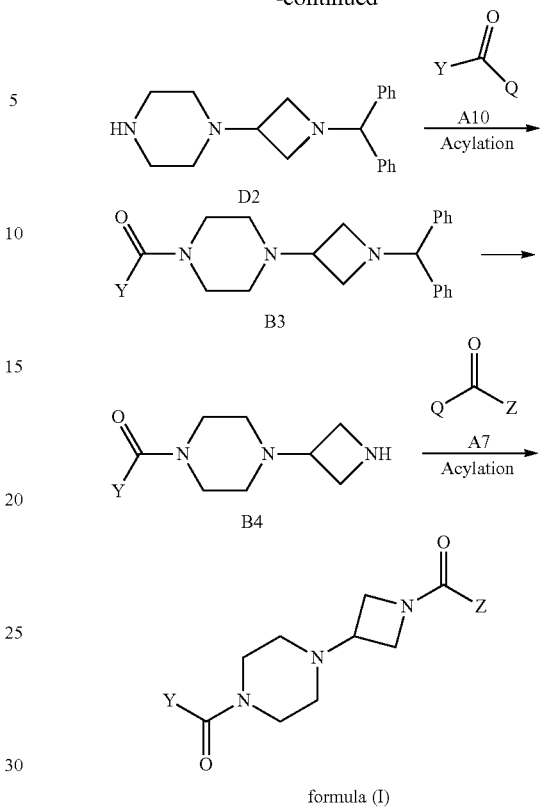

A compound of formula A1 may be treated with a compound of formula A4 to afford a compound of formula D1. Upon conventional removal of protecting group PG, a compound of formula D2 may be coupled with a compound of formula A10 (wherein Q is OH) in the presence of a coupling agent such as HATU, DCC, EDC, HBTU, PyBrOP, and the like; optionally in the presence of a base such as DIPEA to afford a compound of formula B3. When the acylation is effected by the addition of the corresponding acid chloride, the addition of a non nucleophilic base such as pyridine affords a compound of formula B3. Removal of the benzhydryl group as previously described, or, alternatively, by hydrogenation in the presence of a palladium catalyst, affords the corresponding amine, B4. Acylation of a compound of formula B4 with a compound of formula A7 affords a compound of formula (I).

One skilled in the art will recognize that the synthetic sequences of Schemes A, B, C and D may be altered so that the acylation with a compound of formula A7 precedes removal of the benzhydryl group, which is then followed by acylation with a compound of formula A10, thus reversing the order for introduction of groups Y and Z.

Example 1

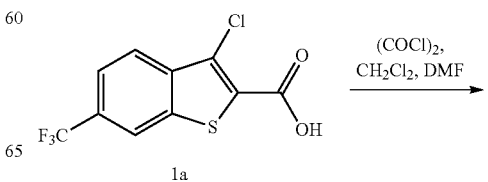

-continued

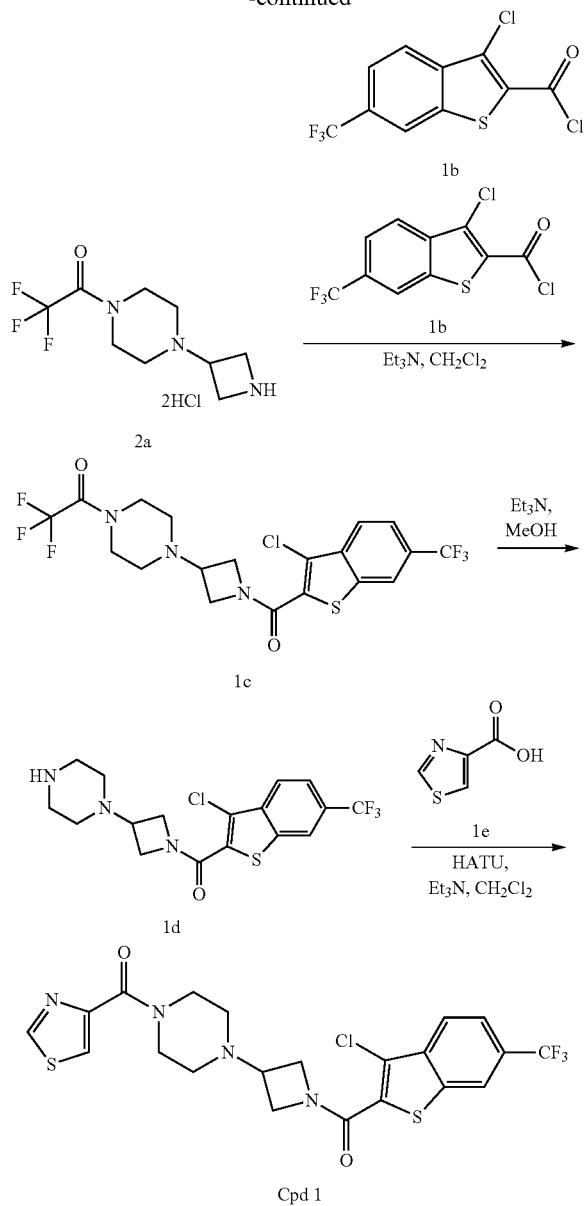

A. 6-Trifluoromethyl-3-chloro-benzo[b]thiophene-2-carbonyl chloride, 1b

To compound 1a (0.205 g, 0.73 mmol) in $CH_2Cl_2$ (7 mL) at room temperature was added $(COCl)_2$ (0.077 mL, 0.88 mmol), followed by 2 drops of DMF. The reaction mixture was stirred at room temperature for 6 h. The reaction mixture was then concentrated to give compound 1b, which was used in the next reaction without further purification.

B. 1-{4-[1-(6-Trifluoromethyl-3-chloro-benzo[b]thiophene-2-carbonyl)-azetidin-3-yl]-piperazin-1-yl}-2,2,2-trifluoro-ethanone, 1c To a solution of compound 2a (0.206 g, 0.66 mmol) and $Et_3N$ (0.61 mL, 4.38 mmol) in $CH_2Cl_2$ (5 mL) at 0° C. was added a solution of compound 1b (0.73 mmol) in $CH_2Cl_2$ (3 mL). The reaction mixture was slowly warmed up to room temperature over 18 h. The reaction mixture was diluted with $CH_2Cl_2$ and washed with aq. $NaHCO_3$. The organic layer was dried over $Na_2SO_4$ and concentrated. Purification by flash column chromatography (silica gel, 3% $MeOH/CH_2Cl_2$) gave compound 1c. $^1H$ NMR (400 MHz, $CD_3OD$): δ 8.13 (m, 1H), 8.01 (d, J=8 Hz, 1H), 7.73 (d, J=8 Hz, 1H), 4.32 (m, 2H), 4.18 (m, 1H), 4.13 (m, 1H), 3.80-3.60 (m, 4H), 3.33 (m, 1H), 2.55-2.40 (m, 4H); MS m/z (M+H$^+$) 500.

C. (3-Chloro-6-(trifluoromethyl)benzo[b]thiophen-2-yl)(3-(piperazin-1-yl)azetidin-1-yl)methanone, 1d A solution of compound 1c (0.30 g, 0.60 mmol) in $Et_3N$ (1 mL) and MeOH (9 mL) was stirred at room temperature for 3 days. It was then concentrated to give compound 1d, which was used in the next reaction without further purification.

D. 1-(1-{[3-Chloro-6-(trifluoromethyl)-1-benzothiophen-2-yl]carbonyl}azetidin-3-yl)-4-(1,3-thiazol-4-ylcarbonyl)piperazine, Cpd 1

To a mixture of compound 1d (0.15 mmol), thiazole-4-carboxylic acid 1e (23 mg, 0.18 mmol), and $Et_3N$ (0.09 mL, 0.65 mmol) in $CH_2Cl_2$ (3 mL) at room temperature was added HATU (68 mg, 0.18 mmol). The reaction mixture was stirred at room temperature for 18 h. It was diluted with diethyl ether, washed with aq. $NaHCO_3$ and aq. NaCl, dried over $Na_2SO_4$, filtered, and concentrated. Purification by flash column chromatography (silica gel, 3% $MeOH/CH_2Cl_2$) gave compound 1. $^1H$ NMR (400 MHz, $CD_3OD$): δ 8.80 (d, J=2 Hz, 1H), 8.13 (t, J=0.8 Hz, 1H), 8.03 (d, J=2 Hz, 1H), 8.01 (d, J=8.6 Hz, 1H), 7.73 (dd, J=1.2 Hz, 8.6 Hz, 1H), 4.31 (m, 2H), 4.21 (m, 1H), 4.15 (m, 1H), 4.01 (m, 1H), 3.93 (m, 2H), 3.81 (m, 1H), 3.33 (m, 1H), 2.55-2.40 (m, 4H); MS m/z (M+H$^+$) 515.

BIOLOGICAL EXAMPLES

In Vitro Methods

Example 1

MGL Enzyme Activity Assay

All rate-based assays were performed in black 384-well polypropylene polymerase chain reaction (PCR) microplates (Abgene) in a total volume of 30 μL. Substrate 4-methylumbelliferyl butyrate (4MU-B; Sigma) and either purified mutant MGL (mut-MGLL 11-313 L179S L186S) or purified wild type MGL (wt-MGLL 6H-11-313) were diluted separately into 20 mM PIPES buffer (pH=7.0), containing 150 mM NaCl and 0.001% Tween 20. Compounds of formula (I) were pre-dispensed (50 nL) into the microplate using a liquid handling dispenser prior to adding 4MU-B (25 μL of 1.2× solution to a final concentration of 10 μM) followed by enzyme (5 μL of a 6× solution to a final concentration of 5 nM) to initiate the reaction. Final compound concentrations ranged from 17 to 0.0003 μM. The fluorescence change due to 4MU-B cleavage was monitored with excitation and emission wavelengths of 335 and 440 nm, respectively, and a bandwidth of 10 nm (Safire$^2$, Tecan) at 37° C. for 5 min.

The $IC_{50}$ values for compounds of formula (I) were determined using a spreadsheet, i.e., Excel® from Microsoft, from a fit of the equation to the concentration-response plot of the fractional activity as a function of inhibitor concentration.

Biological Data Table 1

| Cpd | MGL mutant inh $IC_{50}$ (μM) | MGL wild type inh $IC_{50}$ (μM) |
|---|---|---|
| 1 | 0.0060 | 0.0121 |

Example 2

2-AG Accumulation Assay

To measure the accumulation of 2-AG due to inhibition of MGL, one g rat brain was homogenized using a Polytron homogenizer (Brinkmann, PT300) in 10 mL of 20 mM HEPES buffer (pH=7.4), containing 125 mM NaCl, 1 mM EDTA, 5 mM KCl and 20 mM glucose. Compounds of formula (I) (10 μM) were pre-incubated with rat brain homogenate (50 mg). After a 15-min incubation time at 37° C., $CaCl_2$ (final concentration=10 mM) was added and then incubated for 15 min at 37° C. in a total volume of 5 mL. The reactions were stopped with 6 mL organic solvent extraction solution of 2:1 chloroform/methanol. Accumulated 2-AG in the organic phase was measured by a HPLC/MS method, according to the following equation:

percent vehicle=(2-AG accumulation in the presence of compound/2-AG accumulation in vehicle)×100.

Biological Data Table 2

| | Rat Brain 2AG % VehCntrl | | | |
|---|---|---|---|---|
| Cpd | (%) @0.01 μM | (%) @0.1 μM | (%) @1 μM | (%) @10 μM |
| 1 | 170 | 438 | 839 | 1059 |

Example 3

MGL ThermoFluor® Assay-Mutant

The ThermoFluor (TF) assay is a 384-well microplate-based binding assay that measures thermal stability of proteins[1,2]. The experiments were carried out using Thermofluor instruments available from Johnson & Johnson Pharmaceutical Research & Development, LLC. TF dye used in all experiments was 1,8-ANS (Invitrogen: A-47). Final TF assay conditions used for MGL studies were 0.07 mg/ml of mutant MGL, 100 μM ANS, 200 mM NaCl, 0.001% Tween-20 in 50 mM PIPES (pH=7.0).

Screening compound plates contained 100% DMSO compound solutions at a single concentration. For follow-up concentration-response studies, compounds were arranged in a pre-dispensed plate (Greiner Bio-one: 781280), wherein compounds were serially diluted in 100% DMSO across 11 columns within a series. Columns 12 and 24 were used as DMSO reference and contained no compound. For both single and multiple compound concentration-response experiments, the compound aliquots (46 nL) were robotically predispensed directly into 384-well black microplates (Abgene: TF-0384/k) using the liquid handler. Following compound dispension, protein and dye solutions were added to achieve the final assay volume of 3 μL. The assay solutions were overlayed with 1 μL of silicone oil (Fluka, type DC 200: 85411) to prevent evaporation.

Bar-coded microplates were robotically loaded onto a thermostatically controlled PCR-type thermal block and then heated from 40 to 90° C. degrees at a ramp-rate of 1° C./min for all experiments. Fluorescence was measured by continuous illumination with UV light (Hamamatsu LC6), supplied via fiber optics and filtered through a band-pass filter (380-400 nm; >60D cutoff). Fluorescence emission of the entire 384-well plate was detected by measuring light intensity using a CCD camera (Sensys, Roper Scientific) filtered to detect 500±25 nm, resulting in simultaneous and independent readings of all 384 wells. A single image with 20-sec exposure time was collected at each temperature, and the sum of the pixel intensity in a given area of the assay plate was recorded vs temperature and fit to standard equations to yield the $T_m$[1].

1. Pantoliano, M. W., Petrella, E. C., Kwasnoski, J. D., Lobanov, V. S., Myslik, J., Graf, E., Carver, T., Asel, E., Springer, B. A., Lane, P., and Salemme, F. R. (2001) *J Biomol Screen* 6, 429-40.
2. Matulis, D., Kranz, J. K., Salemme, F. R., and Todd, M. J. (2005) *Biochemistry* 44, 5258-66.

Biological Data Table 3

| Cpd | MGL mutant ThermoFluor Kd (μM) |
|---|---|
| 1 | 0.00193 |

In Vivo Methods

Genetic and environmental factors play a role in the development of obesity and diet is one of the main environmental factors that contribute to this disease. Human studies have shown that increased fat intake is associated with body weight gain that can lead to obesity and other related metabolic diseases. Rodent models fed high-fat diets are therefore useful tools for studying obesity as they will readily gain weight. (Buettner R. et al. *Obesity* (Silver Spring), 2007, 15, 798-808; van Heek, M. et al. *J Clin Invest*, 1997, 99, 385-390). In addition, the high-fat diet*fed rodent model is a useful model to study impaired glucose tolerance and early type 2 diabetes (Soerhede-Winzell, M., *Diabetes, December* 2004, 53(3), S215-S219). This model has been used for studies on pathophysiology and development of new treatments for diabetes, including DPP-IV inhibition and PPAR agonism, both of which were associated with improved insulin secretion in rodents and humans.

Example 4

Effects of Acute MGL Inhibitor Treatment on Food Intake with High-Fat Diet Induced Obese Rodents Obesity is induced by a high-fat diet that derived approximately 45% calories from fat (D-12451; Research Diets Inc.) in rodents for 14 weeks beginning at the age of 7-8 weeks. Obese animals are randomized by body weight and fat mass. The obese rodents are orally treated with vehicle, or vehicle with MGL inhibitor (3, 10 or 30 mg/kg), po bid for 5 days. Food intake is continuously monitored for 4 days and body weight is measured using the BioDAQ food and water intake monitor. On treatment day 5, compound concentrations are measured at 1.5 and 7 hours post dose. Rodents are sacrificed and the following end points are measured: Plasma, intestine and brain monoacylglycerol.

Example 5

Effects of Chronic MGL Inhibitor Treatment on High-Fat Diet Induced Obesity and Insulin Resistance in Rodents Obesity and insulin resistance is induced by a high-fat diet that derives approximately 45% calories from fat (D-12451; Research Diets Inc.) in rodents for 12 weeks at age of 7-8 weeks. Control rodents are fed a 10% low fat diet (D-12450B, Research Diets). Obese rodents are randomized by body weight and fat mass. The obese are orally treated with vehicle, vehicle and rimonabant (10 mg/kg) or vehicle and MGL inhibitor (3, 10 or 30 mg/kg), po bid for 28 days. On day 18, Insulin Tolerance Tests (ITT) are performed. Rodents are fasted for 4 h, and injected intraperitoneal with insulin (0.75 units/kg) and blood samples are taken at 0, 15, 30, 120 and 180 min. On day 22, glucose tolerance tests (OGTT) are performed. Rodents are fasted for 6 h, and injected i.p. with 20% glucose (1.5 g/kg). Blood samples are taken at 0, 15, 30, 120, and 180 min. At the end of treatment, rodents are sacrificed and the following end points are measured: body weight; MRI for body fat and lean composition (also performed at the start of the study); weight of fat pads (epididymal, brown retroperitoneal and subcutaneous); plasma concentrations of HDL-C, LDL-C, total cholesterol, triglycerides, glycerol, PYY, POMC, CART, ghrelin, NPY, free fatty acids, insulin and adipokines (leptin and adiponectin), and endocannabinoids. In addition, tissues (intestine, brain, liver, adipose) are collected for measuring monoacylglycerides and endocannabinoid levels. Anorexic (PYY, POMC, CART) and orexigenic peptides (ghrelin, NPY) are measured in brain. Lipid content is measured in liver. Indirect calorimetry measurements ($VO_2$, $VCO_2$, RQ, energy expenditure, and activity) are performed during week 1 and again at week 11 using a Columbus Instruments Oxymax calorimeter.

While the foregoing specification teaches the principles of the present invention, with examples provided for the purpose of illustration, it will be understood that the practice of the invention encompasses all of the usual variations, adaptations and/or modifications as come within the scope of the following claims and their equivalents.

We claim:

1. A method for treating a patient suffering from obesity, said method comprising administering to a subject in need thereof, a therapeutically effective amount of a compound of formula (I)

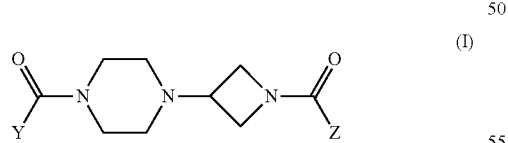

or an enantiomer, diastereomer, solvate, or pharmaceutically acceptable salt thereof;
wherein:
Y is a heteroaryl selected from the group consisting of thienyl, furanyl, thiazolyl, isothiazolyl, oxazolyl, pyridinyl, isoxazolyl, imidazolyl, furazan-3-yl, pyrazolyl, triazolyl, tetrazolyl, and [1,2,3]thiadiazolyl;
wherein Y is optionally independently substituted with one to two substituents selected from the group consisting of fluoro, chloro, bromo, $C_{1-4}$alkyl, cyano, and trifluoromethyl;
Z is a heteroaryl selected from the group consisting of indolyl, indazolyl, benzoxazolyl, benzothiazolyl, benzothienyl, benzofuranyl, imidazo[1,2-a]pyridin-2-yl, pyrrolo[2,3-b]pyridinyl, pyrrolo[3,2-b]pyridinyl, thieno[2,3-b]pyridinyl, quinolinyl, quinazolinyl, and benzimidazolyl;
wherein said Z is optionally independently substituted with one to two substituents selected from the group consisting of $C_{1-4}$alkyl, trifluoromethyl, 2,2,2-trifluoroethoxymethyl, 2,2,2-trifluoroethoxy, trifluoromethylthio, chloro, fluoro, bromo, and iodo;
with the proviso that a compound of formula (I) is other than a compound wherein Y is thiazol-4-yl and Z is 5-fluoro-3H-benzimidazol-2-yl; a compound wherein Y is thiazol-2-yl and Z is 5-fluoro-1H-benzimidazol-2-yl;
a compound wherein Y is thiazol-4-yl and Z is 5-chloro-benzofuran-2-yl; a compound wherein Y is isothiazol-5-yl and Z is 6-trifluoromethyl-1H-indol-2-yl; a compound wherein Y is thiazol-4-yl and Z is 5-trifluoromethyl-1H-pyrrolo[3,2-b]pyridin-2-yl; a compound wherein Y is thiazol-2-yl and Z is 8-bromo-6-chloro-imidazo[1,2-a]pyridin-2-yl; or a compound wherein Y is thiazol-2-yl and Z is 6-trifluoromethyl-imidazo[1,2-a]pyridin-2-yl.

2. A method of treating obesity comprising administering to a subject in need thereof, a therapeutically effective amount of a compound of formula (I)

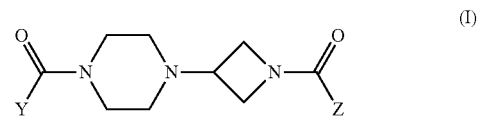

or an enantiomer, diastereomer, solvate, or pharmaceutically acceptable salt thereof;
wherein:
Y is a heteroaryl selected from the group consisting of thienyl, furanyl, thiazolyl, and isothiazolyl;
wherein Y is optionally substituted with one to two substituents independently selected from the group consisting of fluoro, chloro, bromo, and trifluoromethyl;
Z is a heteroaryl selected from the group consisting of indolyl, benzothiazolyl, benzothienyl, pyrrolo[2,3-b]pyridinyl, and thieno[2,3-b]pyridinyl;
wherein Z is optionally independently substituted with one to two substituents selected from the group consisting of $C_{1-4}$alkyl, trifluoromethyl, 2,2,2-trifluoroethoxy-methyl, 2,2,2-trifluoroethoxy, chloro, fluoro, bromo, and iodo;
with the proviso that a compound of formula (I) is other than a compound wherein Y is isothiazol-5-yl and Z is 6-trifluoromethyl-1H-indol-2-yl.

3. A method of treating obesity comprising administering to a subject in need thereof, a pharmaceutical composition comprising a pharmaceutically acceptable carrier and a therapeutically effective amount of a compound of formula (I)

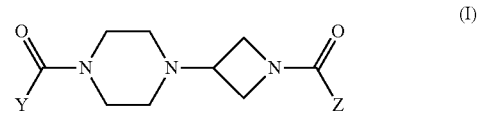

or an enantiomer, diastereomer, solvate, or pharmaceutically acceptable salt thereof;
wherein:
Y is a heteroaryl selected from the group consisting of thienyl, furanyl, thiazolyl, and isothiazolyl;
wherein Y is optionally substituted with one to two substituents independently selected from the group consisting of fluoro, chloro, bromo, and trifluoromethyl;
Z is a heteroaryl selected from the group consisting of indolyl, benzothiazolyl, benzothienyl, pyrrolo[2,3-b]pyridinyl, and thieno[2,3-b]pyridinyl;
wherein Z is optionally independently substituted with one to two substituents selected from the group consisting of $C_{1-4}$alkyl, trifluoromethyl, 2,2,2-trifluoroethoxy-methyl, 2,2,2-trifluoroethoxy, chloro, fluoro, bromo, and iodo;
with the proviso that a compound of formula (I) is other than a compound wherein Y is isothiazol-5-yl and Z is 6-trifluoromethyl-1H-indol-2-yl.

4. A method of treating obesity comprising administering to a subject in need thereof, a pharmaceutical composition comprising a pharmaceutically acceptable carrier and a therapeutically effective amount of 1-(1-{[3-chloro-6-(trifluoromethyl)-1-benzothiophen-2-yl]carbonyl}azetidin-3-yl)-4-(1,3-thiazol-4-ylcarbonyl)piperazine

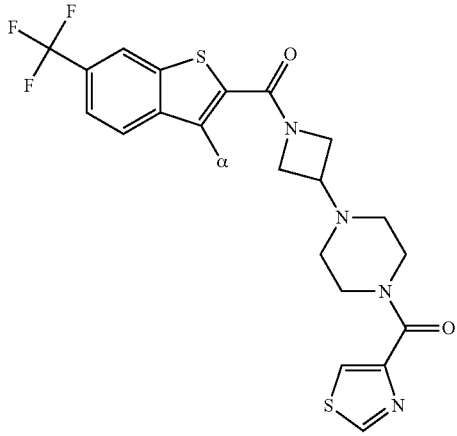

or a solvate or pharmaceutically acceptable salt thereof.

* * * * *